(12) United States Patent
Dorn et al.

(10) Patent No.: US 8,530,160 B2
(45) Date of Patent: Sep. 10, 2013

(54) G-PROTEIN COUPLED RECEPTOR KINASE-5 POLYMORPHISM

(75) Inventors: Gerald W. Dorn, Hamilton, OH (US); Stephen B. Liggett, Clarksville, MD (US)

(73) Assignee: University of Cincinnati, Cincinnati, OH (US)

( * ) Notice: Subject to any disclaimer, the term of this patent is extended or adjusted under 35 U.S.C. 154(b) by 14 days.

(21) Appl. No.: 12/440,296

(22) PCT Filed: Sep. 10, 2007

(86) PCT No.: PCT/US2007/019754
§ 371 (c)(1),
(2), (4) Date: Mar. 6, 2009

(87) PCT Pub. No.: WO2008/030627
PCT Pub. Date: Mar. 13, 2008

(65) Prior Publication Data
US 2010/0248976 A1    Sep. 30, 2010

Related U.S. Application Data

(60) Provisional application No. 60/843,239, filed on Sep. 8, 2006.

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC ....... 435/6.11; 435/6.12; 435/91.1; 536/23.1; 536/24.33

(58) Field of Classification Search
None
See application file for complete search history.

(56) References Cited

PUBLICATIONS

GenBank dbSNP entry rs17098707 added build 123 Oct. 28, 2004.*
Kurnik, Daniel et al. GRK5 Gln41 Leu polymoprhism is not assoicated with senstivity to B1-adrenergic blockade in humans. Pharmacogenomics 2009 vol. 10 No. 10 (11 pages).*
Kunapuli, Priya et al. Cloning and expression of GRK5: A member of the G protein coupled receptor kinase family. PNAS 1993 vol. 90 pp. 5588-5592.*
Juppner Functional properties of the PTH/PTHrP receptor. Bone 1995 vol. 17 No. 2 Supplement 39S-42S.*
GenBank dbSNP entry for rs17098707 http://www.ncbi.nlm.nih.goy/projects/SNP/snp_ref.cgi?rs=17098707 added with build 123 on Oct. 28, 2004.*
Vieux et al. BioTechniques 2002 vol. 32 pp. S28-S32.*
Doughty et al. European Heart Journal 1997 vol. 18 No. 560-565.*
International Search Report for PCT/US07/19754, dated Sep. 4, 2008.
Lohse, Martin et al, What is the role of beta adrenergic signaling in heart failure? 2003, Circulation Research, vol. 93, pp. 896-906.

* cited by examiner

*Primary Examiner* — Amanda Haney
(74) *Attorney, Agent, or Firm* — Dinsmore & Shohl LLP (57) ABSTRACT

The present invention is directed to compositions and methods relating to a G-protein coupled receptor kinase-5 polymorphism. The methods include, for example: detecting enhanced desensitization of the beta adrenergic receptor signaling pathway in an individual, assessing partial protection against heart failure progression in an individual, and assessing an individual's response to beta-blocker therapy. The compositions include polynucleotides or fragments thereof of a nucleotide sequence encoding for a G-protein receptor kinase-5 molecule with a thymine at amino acid position 122 and oligonucleotide primers that hybridize thereto.

4 Claims, 5 Drawing Sheets

FIG. 5

G-PROTEIN COUPLED RECEPTOR KINASE-5 POLYMORPHISM

CROSS-REFERENCES TO RELATED APPLICATIONS

This application claims the benefit of U.S. Provisional Application No. 60/843,239, filed Sep. 8, 2006, which is incorporated herein by reference.

GOVERNMENT INTEREST

This invention was made with government support under NIH grant HL077101 awarded by the National Heart, Lung, and Blood Institute. The government has certain rights in the invention.

FIELD

The present invention is directed to compositions and methods relating to a G-protein coupled receptor kinase-5 polymorphism.

BACKGROUND

Heart associated conditions plague many people. In fact, nearly 5 million Americans are living with heart failure and 550,000 new cases are diagnosed each year. While new medications are continually being developed, there are still many mysteries surrounding why certain people respond better to one medication versus another or why some people develop heart problems earlier than another. As such, there is a need for compositions and methods which can help predict a person's response to particular drug therapy and his/her risk for developing heart disease at an earlier age.

SUMMARY

One embodiment is directed to a method for detecting enhanced desensitization of the beta adrenergic receptor signaling pathway in an individual. The method includes obtaining a sample comprising a polynucleotide encoding a G-protein coupled receptor kinase 5 molecule or a fragment of the polynucleotide from the individual, and determining if the polynucleotide or fragment contains a polymorphic site which results in a leucine at amino acid position 41, wherein the presence of leucine at the polymorphic site indicates an enhanced desensitization of the beta adrenergic receptor signaling pathway.

Another embodiment is directed to a method for assessing partial protection against heart failure progression in an individual. The method includes obtaining a sample comprising a polynucleotide encoding a G-protein coupled receptor kinase 5 molecule or a fragment of the polynucleotide from the individual and determining if the polynucleotide or fragment contains a polymorphic site which results in a leucine at amino acid position 41, wherein the presence of leucine at the polymorphic site indicates partial protection against heart failure progression in the individual.

A third embodiment is directed to a method of assessing an individual's response to beta-blocker therapy. The method includes obtaining a sample comprising a polynucleotide encoding a G-protein coupled receptor kinase 5 molecule or a fragment of the polynucleotide from the individual and determining if the polynucleotide or fragment contains a polymorphic site which results in a leucine at amino acid position 41, wherein the presence of leucine at the polymorphic site indicates a reduced responsiveness to beta-blocker therapy.

An additional embodiment is directed to a polynucleotide or fragment thereof of a nucleotide sequence encoding a G-protein coupled receptor kinase 5 molecule comprising a thymine at nucleotide position 122.

Another embodiment is directed to an oligonucleotide primer that hybridizes to a polynucleotide encoding a G-protein coupled receptor kinase 5 or a fragment of the polynucleotide, wherein the polynucleotide or fragment thereof comprises a thymine at nucleotide position 122.

Additional embodiments, objects and advantages of the invention will become more fully apparent in the detailed description below.

BRIEF DESCRIPTION OF THE DRAWINGS

The following detailed description will be more fully understood in view of the drawings in which.

The embodiments set forth in the drawings are illustrative in nature and are not intended to be limiting of the invention defined by the claims. Moreover, individual features of the drawings and the invention will be more fully apparent and understood in view of the detailed description.

DETAILED DESCRIPTION

Heart failure is a common and deadly condition that will affect one in five adults, having a one in three chance of dying within a year of diagnosis, and a mortality rate of 60-70% in five years. A clinical challenge in managing heart failure is the heterogeneity of this disease. Even among patients with similar forms of heart failure, as within families with genetic cardiomyopathies, there are variations in clinical characteristics.

Furthermore, within the more common non-familial cardiomyopathies there are clusters of clinical phenotypes and a high degree of variability in outcome, despite similar presentations. These observations have led to the notion that common polymorphisms of genes that regulate cardiac contractility, especially those involved in the hemodynamic compromise of heart failure, can play important roles in risk, prognosis and response to treatment. Of particular interest has been the potential for pharmacogenomic effects to modify the therapeutic response to pharmacological β-adrenergic receptor (βAR) antagonism, i.e. β-blockade, in heart failure, which in clinical trials has shown group-mean effects of mortality reduction, but a high degree of individual variability.

Postulated mechanisms for the benefits of (β-blockade in heart failure include protecting the failing heart from toxic effects of circulating catecholamines and partially "resensitizing" myocardial β-adrenergic receptors that have been desensitized. Densensitization is the time-dependent loss of receptor responsiveness to agonist, and is normally a feedback mechanism that protects cells from unregulated over stimulation. Mechanistically, activated receptors are phosphorylated by G-protein coupled receptor kinases (GRKs), which uncouple receptors from their G-protein effectors (densensitization), and participate in the net loss of receptors (downregulation). Indeed, cardiac $β_1$- and $β_2$AR are markedly desensitized and/or downregulated in human heart failure, attributable to high levels of circulating catecholamines. Intriguingly, myocardial GRK activity is increased in human heart failure, and reversing GRK effects is thus a proposed heart failure treatment.

It was therefore believed that functionally significant genetic polymorphisms of myocardial GRKs that target βAR impact cardiac responsiveness to catecholamines and/or the therapeutic response to β-blockade in heart failure. A non-synonymous polymorphism of GRK5 that changes the amino acid at position 41 from glutamine (Q, the most common allele) to leucine (L) was discovered (GRK5-L41). The change resulted from a polymorphism at nucleotide position 122 where an adenine was changed to a thymine. The change to leucine at amino acid position 41 shows a gain-of-function for the kinase, resulting in diminished βAR signaling, and conferring protection against early death in human heart failure to a similar extent as β-blockade.

In the case-control study (explained more fully in the Examples), GRK5-L41 was ~9-fold more common in blacks vs. whites, was not increased in heart failure, but was associated with delayed heart failure onset in blacks (P=0.001), suggesting a protective effect. In comparison with GRK5Q41, GRK5-L41 enhanced desensitization of βAR signaling and cardiac function in CHO cells and transgenic mice, revealing a β-blockage-like attenuation of βAR pathways. In the prospective study, GRK5-Q41 patients were receiving β-blockers. This degree of protection was similar to GRK-L41 patients not receiving β-blockers (RR=0.29, 95% CI=0.11-0.78), vs. Q41 β-blocker nave patients; survival in L41 patients was not further improved by β-blockers. Thus, the GRK5-L41 polymorphism is a genetic equivalent to β-blockade in heart failure and improves outcome and genotyping should identify patients for tailored therapy, particularly those intolerant to β-blocker titration.

As used throughout the specification, the term fragment refers to a portion of the nucleotide sequence for G-protein coupled receptor kinase 5 (SEQ ID NO: 1) which incorporates the nucleotide position 122 or a portion of the protein sequence for G-protein coupled receptor kinase 5 (Accession number NP_005299.1 in NCBI GenBank) which incorporates amino acid position 41. The protein sequence identified as accession number NP_005299.1 in NCBI GenBank database is incorporate herein by reference.

As such, one embodiment of the present invention is directed to a method for detecting enhanced desensitization of the beta adrenergic receptor signaling pathway in an individual, comprising obtaining a sample comprising a polynucleotide encoding a G-protein coupled receptor kinase 5 molecule or a fragment of the polynucleotide from the individual, and determining if the polynucleotide or fragment contains a polymorphic site which results in a leucine at amino acid position 41, wherein the presence of leucine at the polymorphic site indicates an enhanced desensitization of the beta adrenergic receptor signaling pathway. The sample is selected from the group consisting of whole blood, blood serum, blood plasma, urine and saliva. In a very specific embodiment, the sample is whole blood. In a further embodiment, the polymorphic site is located at nucleotide position 122. In another embodiment, the polymorphism change at the nucleotide position is from an adenine to a thymine. In an additional embodiment, the change at amino acid position 41 is from a glutamine to a leucine. In another embodiment, the polynucleotide encoding a G-protein coupled receptor kinase 5 molecule or fragment of the polynucleotide comprises SEQ ID NO: 1.

Another embodiment includes a method for assessing partial protection against heart failure progression in an individual, comprising: obtaining a sample comprising a polynucleotide encoding a G-protein coupled receptor kinase 5 molecule or a fragment of the polynucleotide from the individual, and determining if the polynucleotide or fragment contains a polymorphic site which results in a leucine at amino acid position 41, wherein the presence of leucine at the polymorphic site indicates partial protection against heart failure progression in the individual. In a further embodiment, the polymorphic site is located at nucleotide position 122. In another embodiment, the polymorphism change at the nucleotide position is from an adenine to a thymine. In an additional embodiment, the change at amino acid position 41 is from a glutamine to a leucine. In another embodiment, the polynucleotide encoding a G-protein coupled receptor kinase 5 molecule or fragment of the polynucleotide comprises SEQ ID NO: 1.

An additional embodiment includes a method of assessing an individual's response to beta-blocker therapy, comprising obtaining a sample comprising a polynucleotide encoding a G-protein coupled receptor kinase 5 molecule or a fragment of the polynucleotide from the individual, and b) determining if the polynucleotide or fragment contains a polymorphic site which results in a leucine at amino acid position 41, wherein the presence of leucine at the polymorphic site indicates a reduced responsiveness to beta-blocker therapy. In a further embodiment, the polymorphic site is located at nucleotide position 122. In another embodiment, the polymorphism change at the nucleotide position is from an adenine to a thymine. In an additional embodiment, the change at amino acid position 41 is from a glutamine to a leucine. In another embodiment, the polynucleotide encoding a G-protein coupled receptor kinase 5 molecule or fragment of the polynucleotide comprises SEQ ID NO: 1.

Another embodiment includes a polynucleotide or fragment thereof of a nucleotide sequence encoding a G-protein coupled receptor kinase 5 molecule comprising a thymine at nucleotide position 122. In one embodiment, the thymine at nucleotide position 122 results in a leucine at amino acid position 41 of the corresponding protein. In another embodiment, the polynucleotide or fragment is operable to determine whether an individual with heart failure will have reduced responsiveness to beta-blocker therapy. In an additional embodiment, the polynucleotide or fragment is operable to determine whether an individual has desensitization of beta-adrenergic receptor signaling pathway. In another embodiment, the polynucleotide or fragment is operable to determine whether an individual has partial protection, against heart failure progression. In a further embodiment, the polynucleotide comprises SEQ ID NO: 1. In one embodiment, the fragment comprises SEQ ID NO: 34.

Another embodiment includes an oligonucleotide primer that hybridizes to a polynucleotide encoding a G-protein coupled receptor kinase 5 or a fragment thereof, wherein the polynucleotide or fragment thereof comprises a thymine at nucleotide position 122. In one embodiment, the thymine at nucleotide position 122 results in a leucine at amino acid position 41 of the corresponding protein. In another embodiment, the oligonucleotide primer is operable to determine whether an individual with heart failure will have reduced responsiveness to beta-blocker therapy. In an additional embodiment, the oligonucleotide primer is operable to determine whether an individual has desensitization of beta-adrenergic receptor signaling pathway. In another embodiment, the oligonucleotide primer is operable to determine whether an individual has partial protection against heart failure progression. In a further embodiment, the oligonucleotide primer is selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, and combinations thereof. In one embodiment, the oligonucleotide primer comprises SEQ ID NO: 4. In another embodiment, the oligonucleotide primer comprises SEQ ID NO: 5.

The polymorphic site noted above can be detected by any appropriate means. In one embodiment, the detection of the polymorphic site is by microarray, chain terminating sequencing, restriction digestion, allele specific polymerase reaction, single stranded conformational polymorphism analysis, genetic bit analysis, temperature gradient gel electrophoresis, ligase chain reaction, and or ligase/polymerase genetic bit analysis. In a further embodiment, the detection of the polymorphic site is by microarray.

Example

Methods.

The human study protocols are approved and the subjects provide written informed consent. In the case-control study, heart failure patients at University Hospital, Cincinnati are recruited between Jan. 2, 1999 and Dec. 31, 2004. Non-affected controls from Cincinnati have no cardiac disease or related illness by questionnaire and had normal screening echocardiogram, electrocardiogram, and blood chemistry analysis. In the prospective study, heart failure patients of African descent are recruited from the same institution from May 1, 2000 until Dec. 1, 2005. Enrollment criteria for both studies are: age to 18 to 80 years, left ventricular ejection fraction of less than 40%, and New York Heart Association heart failure class II-IV. β-blocker or angiotensin converting enzyme (ACE) inhibitor use are defined as continuous therapy for at least 6 months during any period of study. The decision to treat with β-blockers and the choice of β-blocker is entirely at the discretion of the patients' physicians. Racial classification as ED (white, of European descent) or AD (black, of African descent) is self-reported.

Genotyping.

PCR primers for the sixteen GRK5 coding exons are given in Table 1 (below). Automated sequencing is performed on an Applied Biosystems ABI 3100 Genetic Analyzer in 96 well format, using standard protocols. Multiple sequences are aligned with the reference sequence using SeqScape v2.5, individually verified by one of the investigators.

TABLE 1

| EXON | PRIMERS | SIZE (bp) |
|---|---|---|
| 1 | F: CAGGAATAATGCGGTAGGC (SEQ ID NO: 2) R: CAAGGCAGGAACCCTGAAG (SEQ ID NO: 3) | 371 |
| 2 | F: CCGTCCCTCTGTCTCTCAG (SEQ ID NO: 4) R: GCTCACCCATTTGCCTTAAT (SEQ ID NO: 5) | 286 |
| 3 | F: AGGTGTGGGAATGACAGGA (SEQ ID NO: 6) R: TCACTGATCACAGAGGACCA (SEQ ID NO: 7) | 238 |
| 4 | F: GGGCTGTGAGGTTCTGTAAC (SEQ ID NO: 8) R: GTGGCCTGGCACAGACTTA (SEQ ID NO: 9) | 236 |
| 5 | F: AGATGTACCAGCACCTGGAG (SEQ ID NO: 10) R: GTGCCCTGTATGGTCAGGTG (SEQ ID NO: 11) | 299 |
| 6 | F: ATTTCCAAAGCTGGACACAG (SEQ ID NO: 12) R: TGAAAAATGTGTACCCTCTGC (SEQ ID NO: 13) | 231 |
| 7 | F: CCACTGTTTCCTGTGGATTC (SEQ ID NO: 14) R: GCCAACCCTTTAGGTTGATT (SEQ ID NO: 15) | 217 |
| 8 | F: ACCCCATCCATTCTCTACCT (SEQ ID NO: 16) R: TCTTTGCGGCCTTTCTGTA (SEQ ID NO: 17) | 400 |
| 9 | F: GAGGGAAGTGGAAGTGAGTG (SEQ ID NO: 18) R: TCTGTCTGACTCTGCATCCTC (SEQ ID NO: 19) | 395 |

TABLE 1-continued

| EXON | PRIMERS | SIZE (bp) |
|---|---|---|
| 10 | F: GACCCAGATGCCAGTGTATC (SEQ ID NO: 20)<br>R: CTTTGCTTTCTTGGGGTTG (SEQ ID NO: 21) | 165 |
| 11 | F: ACAGATGAGAATGCCGAGAG (SEQ ID NO: 22)<br>R: CAGGTGGTGGGTCTCAAG (SEQ ID NO: 23) | 245 |
| 12 | F: CTGTCTCCCTCCTCCTCACT (SEQ ID NO: 24)<br>R: TTCAGCCTGTTTGCTGTTCT (SEQ ID NO: 25) | 348 |
| 13 | F: ATGGTGCAGACACTGTGGAG (SEQ ID NO: 26)<br>R: ACTGTGAGGCAGCACTCG (SEQ ID NO: 27) | 300 |
| 14 | F: CTTCTGCTCCCCAAAACC (SEQ ID NO: 28)<br>R: CTCCTTCCACCCGTCAGT (SEQ ID NO: 29) | 290 |
| 15 | F: GCCTTCCAAGGGTCTCTAC (SEQ ID NO: 30)<br>R: CCGTCCCTCTGTCTCAG (SEQ ID NO: 31) | 292 |
| 16 | F: GCTCCCAGGACTGACTTCT (SEQ ID NO: 32)<br>R: GGGCTCCACTACTTCCACTT (SEQ ID NO: 33) | 230 |

F = forward primer; R = reverse primer

Transgenic Mice.

Transgenic mice expressing human GRK5-Q41 and MI are generated using standard methods. Mouse lines with equivalent cardiac GRK5-Q41 and GRK5-L41 protein expression (antibodies from Santa Cruz) are propagated for study. Animals are treated in accordance with approved University of Cincinnati Animal Care and Use Committee protocols.

In Vitro and In Vivo βAR Desensitization Studies.

Isoproterenol-stimulated accumulation of cAMP in transfected Chinese Hamster Ovary (CHO) cells is assayed as previously described. In mice, M-mode echocardiograms, cardiac catheterization, myocardial gene expression, and cardiac histology studies are performed as described. To assess βAR responsiveness and desensitization, mice are studied by left ventricular catheterization during graded infusions of the nonselective a-agonist isoproterenol, 0.1 to 3.2 ng/g/min, and 20 ng/g/min to evoke desensitization. Basal, isoproterenol and NaF-stimulated myocardial adenylyl cyclase activities are determined as described.

Statistical Analysis.

T-tests and chi-square tests are used to assess significant differences in variables between ethnic groups and between genotype classes within ethnic groups. Allele and genotype frequencies are calculated using standard gene-counting techniques. Hardy-Weinberg Equilibriums (HWE) are assessed in each ethnic group separately, using a chi-square test or Fisher's Exact test if a genotype class had less than 5 individuals. Differences in time from enrollment to death or cardiac transplant between different genotype classes are assessed using Kaplan-Meier curves and Log Rank tests. Relative risks are obtained using Cox Proportional Hazards modeling and are calculated after adjustment for age at initial clinic visit, β-blocker usage, hypertension status, and sex. An alpha level of 0.05 is used to asses the significance of statistical tests. All analyses are carried out using the R Statistical Language. Contractility of isoproterenol-infused mouse hearts (max+dP/dt) is compared by 1-way ANOVA at each time point and significance is taken at $P<0.05$, with Tukey's post-hoc test to identify pairwise differences, unless otherwise indicated.

Results—GRK5, but not GRK2, Displays Genetic Variability.

The 16 exons of GRK5 are resequenced in 96 individuals to ascertain variations. Four non-synonymous variations at nucleic acid positions 122 (A/T), 840 (G/A), 1274 (C/T) and 1624 (C/G) are detected, corresponding to amino acid changes from the major allele at residues 41 (Q to L), 304 (R to H), 425 (T to M) and 542 (P to A) (Table 2—below). The GRK5-Q41L variant is the only one with an allele frequency >0.05, and is therefore the focus of further genotyping. There are no non-synonymous polymorphisms of the GRK2 coding exons found.

TABLE 2

| Nucleotide | Amino Acid | Minor Allele Frequency (%) ED | Minor Allele Frequency (%) AD |
|---|---|---|---|
| 122 A/T | Q41L | 2.0 | 15.6 |
| 840 G/A | R304H | 1.0 | 0.0 |
| 1274 C/T | T425M | 0.0 | 2.0 |
| 1624 C/G | P542A | 1.0 | 0.0 |

Case-Control Study of GRK5-Q41L in Heart Failure.

As β-adrenergic signaling is regulated by GRKs, it is critical for minute-by-minute control of normal cardiac function, and can be a pathological mediator in failing hearts. Additionally, it is believed that the GRK5-L41 polymorphism influences susceptibility to, or progression of, heart failure. To test this, a cohort of normal individuals and heart failure patients followed at the University of Cincinnati are genotyped (Table 3—below). This population is utilized primarily to ascertain disease risk in a case-control fashion, and to identify trends in disease modification. The unaffected population consists of 533 subjects (470 ED of mean age 49.3 years and 63 AD of mean age 47.8 years) with negative histories and physical examinations for heart failure, and with normal ECGs and echocardiograms. In this control group, the allele frequency of the L41 variant is 0.013 in the ED population and 0.25 in the AD population. By comparison, ED heart failure subjects have an L41 allele frequency of 0.024 and AD heart failure subjects have an M1 allele frequency of 0.238, which are not different than the respective allele frequencies in unaffected controls. Among AD heart failure patients, in which the polymorphism is more common, the heterozygous genotype frequency is 0.351 and the homozygous L41 frequency is 0.062. These allele distributions are consistent with predictions from Hardy-Weinberg equilibrium ($P>0.5$), and indicate that the GRK5-L41 polymorphism is not associated with increased risk of developing heart failure.

TABLE 3

| | ED | | AD | |
|---|---|---|---|---|
| Variable | N | Mean ± SD | N | Mean ± SD |
| Age at enrollment (yrs) | 568 | 53 ± 13 | 242 | 51 ± 13 |
| Follow-up (yrs) | 558 | 2.3 ± 2.2 | 241 | 2.3 ± 2.1 |
| Height (cm) | 554 | 172 ± 10 | 230 | 172 ± 10 |

TABLE 3-continued

| | | | | |
|---|---|---|---|---|
| Weight (kg) | 560 | 86 ± 21 | 240 | 90 ± 26 |
| Fractional Shortening (%) | 432 | 22 ± 11 | 215 | 22 ± 11 |
| Left Ventricular EF (%) | 401 | 28 ± 14 | 142 | 33 ± 15 |
| Left Ventricular Mass/BSA | 395 | 191 ± 69 | 197 | 183 ± 63 |
| Variable | N | % | N | % |
| Males | 394 | 69.3 | 133 | 55.0 |
| Diagnosis | | | | |
| Other | 67 | 12.0 | 42 | 17.6 |
| CAD | 184 | 33.0 | 37 | 15.5 |
| IDC | 306 | 54.9 | 159 | 66.8 |
| Hypertension | 256 | 45.1 | 194 | 80.2 |
| β blocker use | 387 | 69.2 | 194 | 80.2 |
| Had cardiac transplant | 161 | 28.3 | 18 | 7.4 |

Figure 1:
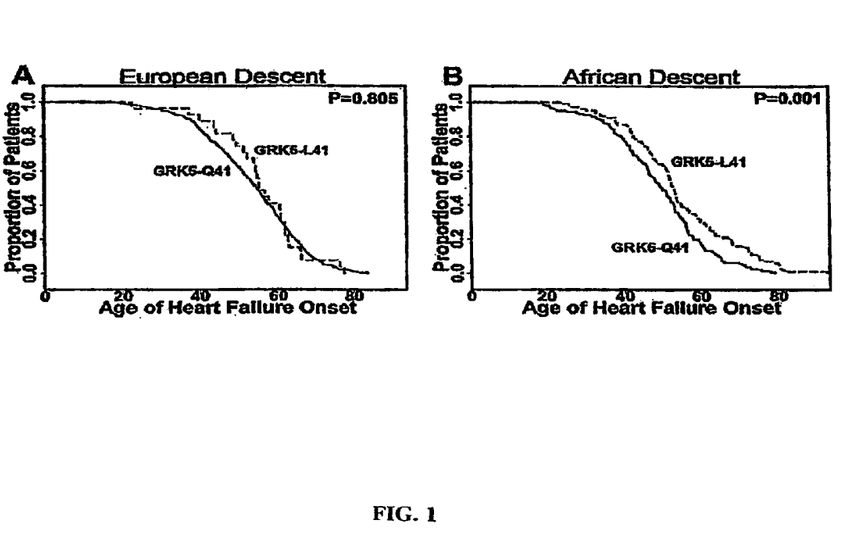
FIG. 1 is a set of graphs depicting heart failure onset in GRK5-Q41 and L41 subjects using Kaplan-Meier curves for heart failure subjects comparing GRK5-L41 carriers versus GRK5-Q41 homozygotes for age of diagnosis in 568 patients of European descent (A) and 242 patients of African descent (B)

Within the group of heart failure cases, Kaplan-Meier methods and Cox Proportional Hazards modeling are undertaken for heart failure progression, defined by the end points of death or cardiac transplantation. To avoid spurious associations resulting from the differences in allele frequencies between AD and ED, these populations are analyzed separately. The initial comparison examines clinical parameters at study entry of patients homozygous for the wild-type Q41 vs. those who are carriers for the L41 polymorphism (heterozygotes and homozygotes combined). Baseline characteristics listed in Table 3 are not different between those with or without GRK5-L41 (data not shown). In the ED cohort, there are no genotype differences in time to development of heart failure (P=0.805, FIG. 1A) or survival time after heart failure development (P=0.884). In contrast, while carriers of the L41 allele in the AD cohort also did not have a significant difference in survival after heart failure development compared to Q41 homozygotes (P=0.336), they developed heart failure at a significantly later age than Q41 homozygotes (FIG. 1B, P=0.001). This suggests that the amino acid substitution conferred by the polymorphism provides partial protection against heart failure progression to death or transplantation by altering GRK5 function in this population.

GRK5-Q41 and L41 Differentially Affect $\beta_1$-Adrenergic Receptor Desensitization in Transfected CHO Cells.

Figure 2:
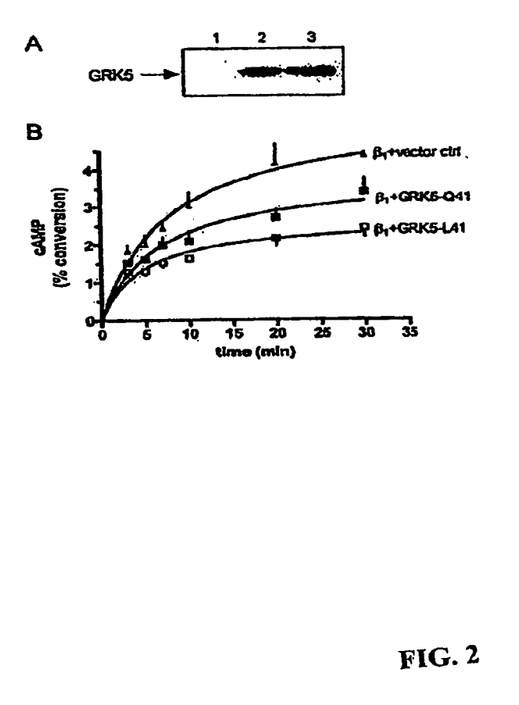
FIG. 2A is an immunoblot analysis of GRK5 in control-(lane 1), Q41-(lane 2), and L41-(lane 3) transfected CHO cells
FIG. 2B is a graph showing time dependent accumulation of cAMP in GRK5 transfected cells stimulated with 10 µM isoproterenol, both of which show differential effects of GRK-Q41 and L41 on β-adrenergic receptor desensitization.

To determine whether the GRK5-Q41L polymorphism alters receptor signaling in a pathway relevant to heart failure, its effects on $\beta_1$AR desensitization during continuous agonist exposure are investigated using a previously validated in vitro model. CHO cells are co-transfected with human $\beta_1$AR (Arg389 variant, which is the most common) and either GRK5-Q41 or GRK5-L41. Receptor expression (determined by radioligand binding, data not shown) and GRIP expression as determined by Western blotting (FIG. 2A) are equivalent. Cells are exposed to 10 µM isoproterenol for various times, and the time course for accumulation of intracellular cAMP quantitated. As shown in FIG. 2B, GRK5-L4I cells have diminished response compared to GRK-Q41 (P<0.001 by ANOVA), with decreased maximal response (2.6±0.2 vs 3.8±0.4, P<0.05) and a depressed rate of cAMP accumulation (4.7±1.2 vs 6.4±1.9, P<0.05) compared to GRK5-Q41 cells. This finding reveals enhanced agonist-promoted, GRK5-mediated, desensitization of $\beta_1$AR in this model system.

GRK5-L41 is Similar to Protection by β-Blockade in Human Heart Failure.

Figure 3:
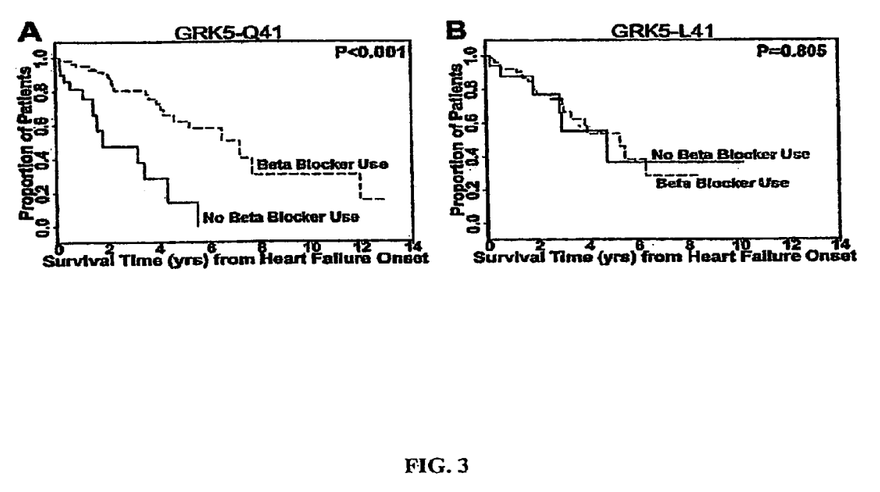
FIG. 3 is a set of graphs depicting prospective analysis of GRK5 polymorphism effects on therapeutic response to β-blockade in 339 AD heart failure patients using Kaplan-Meier curves for time from presentation with heart failure to death or cardiac transplantation for β-blocker users and non-β-blocker users in GRK5-Q41 homozygous (A) and GRK5-L41 carriers (B)

The accumulated human and cell data shows that GRK5-L41: a) is common in individuals of AD, b) confers enhanced desensitization of $\beta_1$-adrenergic receptor signaling, and c) has a protective effect in heart failure. The GRK5-L41 phenotype of attenuated βAR signaling is not unlike that of βAR blockade. Accordingly, it is believed that the protective effect of GRK5-L41 in AD heart failure patients reflects an interaction with pharmacological 13-blockade, and a prospective analysis of AD heart failure patients (n=339) comparing outcome as a function of GRK5-Q41L genotype and β-blocker status is thus performed. This study is restricted to the AD population due to the low frequency of GRK5-L41 in the ED population. As shown in Table 4 (below), there are no significant differences in clinical characteristics between the genotype-stratified groups. Follow-up is for a mean of 1.9 years and 82% are treated with β-blockers (73%—carvedilol, 22%—metoprolol, and 5%—others). Among homozygous Q41 heart failure patients, lack of β-blocker therapy characteristically diminishes survival (P<0.001, FIG. 3A). In contrast, survival in non-β-blocker treated L41 carriers is similar to β-blocker-treated patients regardless of their genotype (Q41 homozygous, P=0.23 1; L41 carriers, P=0.805, FIG. 3B).

TABLE 4

| | AD | |
|---|---|---|
| Variable | GRK5-Q41 | GRK5-L41* |
| Fractional Shortening (%) | 23 ± 12 | 22 ± 11 |
| LV Ejection Fraction (%) | 34 ± 16 | 33 ± 15 |
| Dilated Cardiomyopathy (%) | 64.5 | 66.9 |
| Ischemic Cardiomyopathy (%) | 18.7 | 22.1 |
| LV Mass Indexed to BSA (g) | 177 ± 55 | 188 ± 69 |
| Hypertension (%) | 80.3 | 76.3 |
| Beta Blocker Use (%) | 81.7 | 81.6 |
| ACE Inhibitor Use (%) | 85.6 | 83.8 |
| Female (%) | 31.8 | 31.6 |

*L41 represents heterozygotes or homozygotes

To formally evaluate the potential interaction effect of β-blocker usage and Q41L allele, a Cox Proportional Hazards model for time to death/transplant that included age, sex, hypertension status, β-blocker usage, and Q41L status, with and without an interaction term between β-blocker usage and Q41L status are compared. The model with the interaction term is significantly better than the (educed model as measured by a likelihood ratio test (P=0.007), and the β-blocker-carrier status interaction term is significant at P=0.009, demonstrating for the death/transplant outcome an interaction between GRK5 genotype and β-blocker usage. Using wild-type (GRK5-Q41) non-β-blocker users as the reference group, β-blocker treatment in Q41 reduces the risk of death or cardiac transplantation by 83% (relative risk of 0.17 95% CI=0.08 to 0.35) (Table 5—below). Likewise, in L41 patients treated with β-blockers the risk is decreased by 77% (relative risk of 0.23; 95% CI=0.11 to 0.49), demonstrating equivalent risk with (β-blockade in those with this GRK5 genotype. Strikingly, though, even in the absence of β-blocker treatment, risk of death or transplant in L41 patients is decreased by 71% compared with the wild-type, non-treated population (relative risk of 0.29; 95% CI=0.11 to 0.78). These data indicate that GRK5-L41 carriers with heart failure are intrinsically protected to an extent that is similar to the protection afforded by β-blocker treatment. The potential concern that population stratification within the AD cohort is leading to spurious associations is unlikely, as AD individuals previously recruited from the same geographic region showed no evidence of population stratification.

TABLE 5

| Group | | | | |
|---|---|---|---|---|
| Genotype† | β-blocker | Relative Risk | 95% CI | P-value |
| Q41 | − | 1.0 (reference) | | |
| Q41 | + | 0.17 | 0.08 to 0.35 | <0.001 |
| L41 | − | 0.29 | 0.11 to 0.78 | 0.014 |
| L41 | + | 0.23 | 0.11 to 0.49 | <0.001 |

*P = 0.009 for interaction of GRK5-Q41 status and β-blocker usage.
†L41 represents heterozygotes or homozygotes.

Desensitization of Cardiac β-Adrenergic Receptors in Transgenic Mice is Augmented by GRK-L41.

Figure 4:
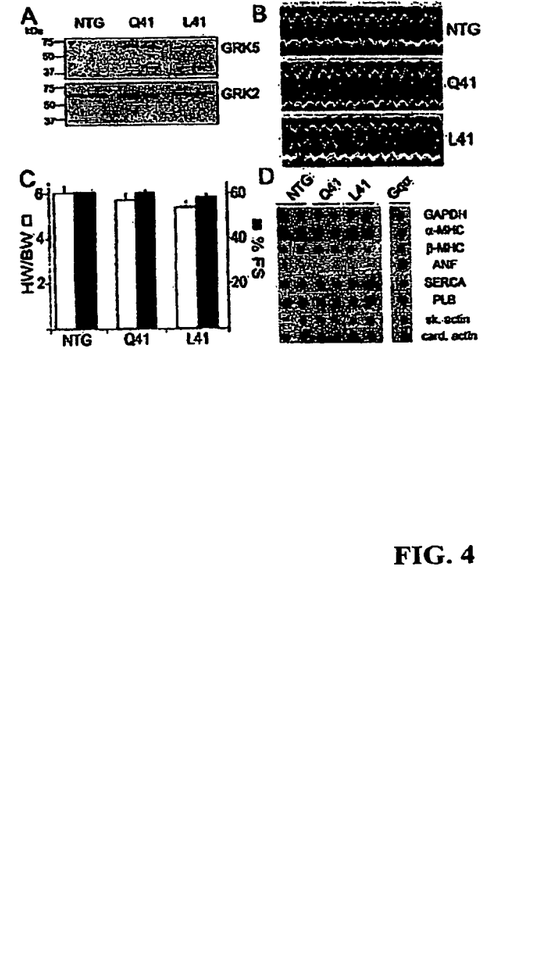
FIG. 4A is an immunoblot analysis of cardiac GRK5 and GRK2 expression levels from matched GRK5-Q41 and GRK5-L41 transgenic mice.
FIG. 4B is representative M-mode echocardiograms.
FIG. 4C is quantitative data for heart weight/body weight (HW/BW, mg/g, white bars) and echocardiographic left ventricular fractional shortening (FS, %, black bars)
FIG. 4D is a RNA dot blot analysis of cardiac genes where Gq transgenic is positive control for pathologic gene expression, GAPDH=glyceraldehyde phospho-dehydrogenase, MHC=myosin heavy chain, ANF=atrial natriuretic factor, SERCA=sarcoplasmic reticulum calcium ATPase, PLB=phospholamban, sk and card actinskeletal and cardiac actin, respectively, all of which show characterization of hearts expressing GRK5-Q41 and GRK5-L41.
Figure 5:
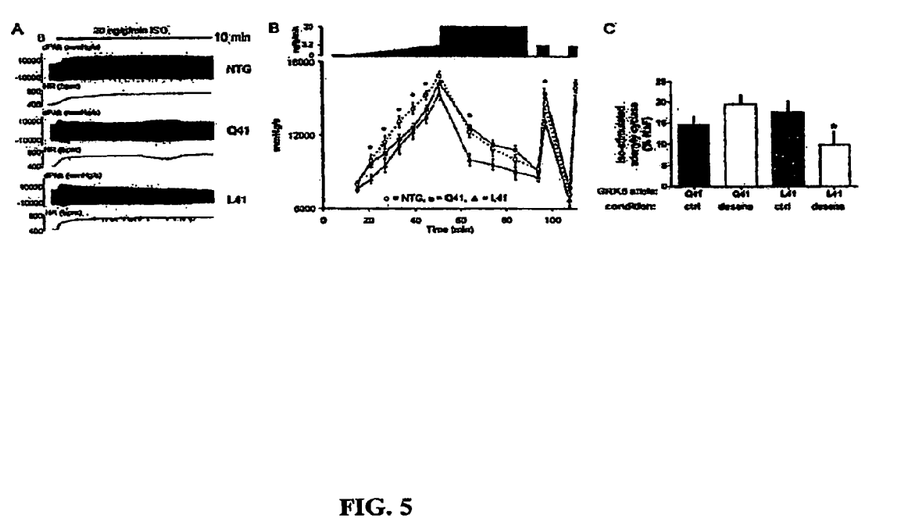
FIG. 5A is a graph showing representative dP/dt and heart rate responses to continuous high-dose intravenous isoproterenol in isolated perfused hearts.
FIG. 5B is a graph showing mean data for sensitivity, desensitization, and resensitization to infused isoproterenol in closed chest in vivo catheterization studies where the top shows isoproterenol dose over time and the bottom is peak positive dP/dt n=12/group.
FIG. 5C is a graph showing adenylyl cyclase activities in isolated perfused hearts desensitized (desens) with isoproterenol, 20 ng/g/min, for 10 minutes, n=4/group where *P<0.05 vs control (ctrl); all showing βAR desensitization response of GRK5-Q41 and L41 transgenic mice to isoproterenol infusion.

GRK5-L41 improves heart failure outcome, enhances desensitization of $\beta_1AR$ in cultured cells, and interacts with β-blockade. Next, the physiologic impact of the GRK5-Q41 and L41 variants on the heart in cardiac transgenic mice is determined. Two lines selected for comparable GRK5 expression levels (FIG. 4A) shows no abnormalities of cardiac size, histological appearance, disease-related gene expression, or basal contractile function (FIGS. 4B-D). To determine the effects of the GRK5 variants on $\beta_1AR$ stimulation of cardiac contractility, mice undergo cardiac catheterization to measure left ventricular peak positive dP/dt at baseline and in response to isoproterenol (FIG. 5). Pre-desensitization receptor function is measured with increasing doses of infused isoproterenol up to 3.2 ng/g/min. Then, receptor desensitization is measured during a continuous 20 ng/g/min isoproterenol infusion over 30 mm. Finally, after 10 minute washout periods, resensitization is determined with bolus infusion of 3.2 ng/g/min isoproterenol. Sensitivity to infused isoproterenol is diminished by either GRK5-Q41 or L41, as indicated by the similar rightward shifts in the dose-response curves, compared with non-transgenic mice (FIG. 5B, P=0.02). In contrast, desensitization after 10 minutes of sustained high-dose isoproterenol infusion is greater (e.g., peak positive dP/dt response is lower) in GRK5-L41 mice than either GRK5-Q41 mice or non-transgenic controls (P<0.001, n=12/group) (FIG. 5A, 5B middle portion of graph). Additionally, resensitization (e.g., recovery of response after washout) is significantly impaired after 10 minutes in the GRK5-L41 mice (P=0.035), and continues to trend so after 20 mm (P=0.066) (FIG. 5B, right-hand side of graph). Isoproterenol stimulates adenylyl cyclase activities and parallels the 10 minute functional desensitization results (FIG. 5C). These data demonstrate direct effects of GRK5 on cardiac function, and for the more active L41 variant, a β-blocker-like attenuation of cardiac adrenergic responses.

DISCUSSION

As introduced earlier, common polymorphisms are proposed as a basis for heart failure risk, disease modification, and the response to therapy. Given the morbidity, mortality and health-care costs of heart failure, there are substantial efforts underway to find genetic markers, or biomarkers, to aid in prognosis and management of these patients. Here, the gene encoding GRK5 is considered because it is positioned at a critical nodal point in the βAR signaling pathway. This candidate is particularly attractive since its role in signaling is to modify receptor number and coupling to G-proteins and signaling effectors such as adenylyl cyclase, i.e., the important parameters of βAR that are perturbed in heart failure. Furthermore, GRK5 likely modifies the signaling through both $\beta_1$- and $\beta_2AR$ receptor subtypes, as well as other critical receptors in heart failure.

The predominant cardiac GRKs are 2 and 5, and the current results suggest that a gain-of-function GRK5 polymorphism which attenuates $\beta_1AR$ function in the setting of heart failure is protective. Although relatively fewer studies have been conducted with GRK5, compared with GRK2 they reveal differences in subcellular localization and trafficking, receptor specificity, fry sensitivity, and the ability to transduce non-G protein-coupled signals. These functional distinctions may explain why the Q to L substitution of GRK5 increases kinase activity and appears to be associated with a survival phenotype in the AD heart failure population. It is recognized that these findings are more likely applicable to the AD population given that the frequency of L41 is ~9-fold greater in the AD vs ED population. Regardless, any individual who demonstrates the polymorphism will benefit.

The foregoing description of various embodiments and principles of the invention has been presented for the purposes of illustration and description. It is not intended to be exhaustive or to limit the inventions to the precise forms disclosed. Many alternatives, modifications, and variations will be apparent to those skilled the art. Moreover, although multiple inventive aspects and principles have been presented, these need not be utilized in combination, and various combinations of inventive aspects and principles are possible in light of the various embodiments provided above. Accordingly, the above description is intended to embrace all possible alternatives, modifications, aspects, combinations, principles, and variations that have been discussed or suggested herein, as well as all others that fall within the principles, spirit and scope of the inventions as defined by the claims.

What is claimed is:

1. A method for treating a human patient diagnosed with heart failure, the method comprising:
   a) obtaining a sample comprising a polynucleotide encoding G-protein coupled receptor kinase 5 (GRK5), or a fragment thereof, from the patient,
   b) treating the sample, under amplification conditions, with a pair of polymerase chain reaction (PCR) primers that hybridize to the polynucleotide, the PCR primers comprising SEQ ID NO: 4 and SEQ ID NO: 5, to provide an amplification product,
   c) sequencing the amplification product of step (b),
   d) identifying the amino acid residue at position 41 of GRK5 based on the sequencing of step (c), and
   e) treating the patient with beta blocker therapy when the patient is homozygous for glutamine at position 41 of GRK5, or treating the patient with a therapy for heart failure that excludes beta blocker therapy when the patient is heterozygous or homozygous for leucine at position 41 of GRK5.

2. The method of claim 1, wherein the polynucleotide comprises a polymorphic site at nucleotide position 353 of SEQ ID NO: 1.

3. A method for treating a human patient diagnosed with heart failure and at risk for death or cardiac transplantation, the method comprising:
   a) obtaining a sample comprising a polynucleotide encoding G-protein coupled receptor kinase 5 (GRK5), or a fragment thereof, from the patient,
   b) treating the sample, under amplification conditions, with a pair of polymerase chain reaction (PCR) primers that hybridize to the polynucleotide, the PCR primers comprising SEQ ID NO: 4 and SEQ ID NO: 5, to provide an amplification product,
   c) sequencing the amplification product of step (b),
   d) identifying the amino acid residue at position 41 of GRK5 based on the sequencing of step (c), and
   e) treating the patient with beta blocker therapy when the patient is homozygous for glutamine at position 41 of GRK5, or treating the patient with a therapy for heart failure that excludes beta blocker therapy when the patient is heterozygous or homozygous for leucine at position 41 of GRK5, wherein the presence of leucine at position 41 of GRK5 indicates that the patient will not live significantly longer if treated with a beta-blocker in comparison to a patient having leucine at position 41 who is not treated with a beta-blocker, and wherein the presence of two glutamines at position 41 of GRK5 indicates that the patient will live significantly longer if treated with a beta-blocker in comparison to a patient having two glutamines at position 41 of GRK5 who is not treated with a beta-blocker.

4. The method of claim 3, wherein the polynucleotide comprises a polymorphic site at nucleotide position 353 of SEQ ID NO: 1.

* * * * *

SEQUENCE LISTING

<160> NUMBER OF SEQ ID NOS: 34

<210> SEQ ID NO 1
<211> LENGTH: 980
<212> TYPE: DNA
<213> ORGANISM: Homo sapiens

<400> SEQUENCE: 1

```
cagccgtggg ggatgcctgg tgtgggtggg gtgcagggga gccctaggcc tcactgctag      60
ggggccgggg tcaggcagga ctgtgcggga tactggggct cacagcccac ctgggaggaa     120
gagtgtgtgt gtttgtgtgt gtcttgggct gggggtgtgt cactggcttg gcctacagcc     180
cgtccctctg tctctcagcc caggaggctg gtgggcaggc tcactgcggg gacgccgcag     240
```

```
gctctggagc ctcagccagg catcttttc cccatctctg caggggggcgg aggaaagcgc      300 aaagggaaaa gcaagaagtg gaaagaaatc ctgaagttcc ctcacattag ccagtgtgaa      360
gacctccgaa ggaccatagg taagctgtcc tgcctggggg ctgtgcgggg agtgagtagc      420
aggtgatccg ccaagccgtt tgtgcattaa ggcaaatggg tgagccgcca agctgtctgt      480
gcagtgaggc aaatgccaat cagtggacac agtattgtgc ttccaggtag ggctccagg      540 ctgacctttt tgctaatcaa cataaacagg caaccagtat tcattgaata tatggcatgt      600
gccgggcaga gtgacctcct cccagttatc atttgaggca ggtgctatta tttaatattt      660
cacttcacct ttcagatggg gaaactgagg cacagagtgg ttctgtaacg gcccaaagtc      720
acacagctga tgggagggtg gtggaggtgg gccaggccca acacagagcc accgctcata      780
acttctcccc tttcttcctg gagcctgtgg gtcctgccct caggggggcag cccaggctt      840 gggagctgag agtcaggtgg ggtgggggat gtggggtgag gtgggggagg tagggctccc      900 cttttccactt gctgggatg tcagtgctcc tgaggagcca ctgggctcag tggcacagct      960 tagcccctg tatccagcac                                                    980
```

```
<210> SEQ ID NO 2
<211> LENGTH: 19
<212> TYPE: DNA
<213> ORGANISM: Homo sapiens

<400> SEQUENCE: 2
caggaataat gcggtcggc                                                     19

<210> SEQ ID NO 3
<211> LENGTH: 19
<212> TYPE: DNA
<213> ORGANISM: Homo sapiens

<400> SEQUENCE: 3
caaggcagga accctgaag                                                     19

<210> SEQ ID NO 4
<211> LENGTH: 20
<212> TYPE: DNA
<213> ORGANISM: Homo sapiens

<400> SEQUENCE: 4
ccgtccctct tgtctctcag                                                    20

<210> SEQ ID NO 5
<211> LENGTH: 19
<212> TYPE: DNA
<213> ORGANISM: Homo sapiens

<400> SEQUENCE: 5
gctcacccat tgccttaat                                                     19

<210> SEQ ID NO 6
<211> LENGTH: 19
<212> TYPE: DNA
<213> ORGANISM: Homo sapiens

<400> SEQUENCE: 6
aggtgtggga atgacagga                                                     19

<210> SEQ ID NO 7
<211> LENGTH: 20
```

```
<212> TYPE: DNA
<213> ORGANISM: Homo sapiens

<400> SEQUENCE: 7
tcactgatca cagaggacca                                              20

<210> SEQ ID NO 8
<211> LENGTH: 20
<212> TYPE: DNA
<213> ORGANISM: Homo sapiens

<400> SEQUENCE: 8
gggctgtgag gttctgtaac                                              20

<210> SEQ ID NO 9
<211> LENGTH: 19
<212> TYPE: DNA
<213> ORGANISM: Homo sapiens

<400> SEQUENCE: 9
gtggcctggc acagactta                                               19

<210> SEQ ID NO 10
<211> LENGTH: 20
<212> TYPE: DNA
<213> ORGANISM: Homo sapiens

<400> SEQUENCE: 10
agatgtacca gcacctggag                                              20

<210> SEQ ID NO 11
<211> LENGTH: 20
<212> TYPE: DNA
<213> ORGANISM: Homo sapiens

<400> SEQUENCE: 11
gtgccctgta tggtcaggtg                                              20

<210> SEQ ID NO 12
<211> LENGTH: 20
<212> TYPE: DNA
<213> ORGANISM: Homo sapiens

<400> SEQUENCE: 12
atttccaaag ctggacacag                                              20

<210> SEQ ID NO 13
<211> LENGTH: 21
<212> TYPE: DNA
<213> ORGANISM: Homo sapiens

<400> SEQUENCE: 13
tgaaaaatgt gtaccctctg c                                            21

<210> SEQ ID NO 14
<211> LENGTH: 20
<212> TYPE: DNA
<213> ORGANISM: Homo sapiens

<400> SEQUENCE: 14
ccactgtttc ctgtggattc                                              20

<210> SEQ ID NO 15
<211> LENGTH: 20
```

-continued

```
<212> TYPE: DNA
<213> ORGANISM: Homo sapiens

<400> SEQUENCE: 15 gccaacccttt taggttgatt                                              20

<210> SEQ ID NO 16
<211> LENGTH: 20
<212> TYPE: DNA
<213> ORGANISM: Homo sapiens

<400> SEQUENCE: 16
accccatcca ttctctacct                                               20

<210> SEQ ID NO 17
<211> LENGTH: 19
<212> TYPE: DNA
<213> ORGANISM: Homo sapiens

<400> SEQUENCE: 17
tctttgcggc ctttctgta                                                19

<210> SEQ ID NO 18
<211> LENGTH: 20
<212> TYPE: DNA
<213> ORGANISM: Homo sapiens

<400> SEQUENCE: 18
gagggaagtg gaagtgagtg                                               20

<210> SEQ ID NO 19
<211> LENGTH: 21
<212> TYPE: DNA
<213> ORGANISM: Homo sapiens

<400> SEQUENCE: 19
tctgtctgac tctgcatcct c                                             21

<210> SEQ ID NO 20
<211> LENGTH: 20
<212> TYPE: DNA
<213> ORGANISM: Homo sapiens

<400> SEQUENCE: 20
gacccagatg ccagtgtatc                                               20

<210> SEQ ID NO 21
<211> LENGTH: 19
<212> TYPE: DNA
<213> ORGANISM: Homo sapiens

<400> SEQUENCE: 21
ctttgctttc ttggggttg                                                19

<210> SEQ ID NO 22
<211> LENGTH: 20
<212> TYPE: DNA
<213> ORGANISM: Homo sapiens

<400> SEQUENCE: 22
acagatgaga atgccgagag                                               20

<210> SEQ ID NO 23
<211> LENGTH: 18
```

```
<212> TYPE: DNA
<213> ORGANISM: Homo sapiens

<400> SEQUENCE: 23
caggtggtgg gtctcaag                                              18

<210> SEQ ID NO 24
<211> LENGTH: 20
<212> TYPE: DNA
<213> ORGANISM: Homo sapiens

<400> SEQUENCE: 24
ctgtctccct cctcctcact                                            20

<210> SEQ ID NO 25
<211> LENGTH: 20
<212> TYPE: DNA
<213> ORGANISM: Homo sapiens

<400> SEQUENCE: 25
ttcagcctgt ttgctgttct                                            20

<210> SEQ ID NO 26
<211> LENGTH: 20
<212> TYPE: DNA
<213> ORGANISM: Homo sapiens

<400> SEQUENCE: 26
atggtgcaga cactgtggag                                            20

<210> SEQ ID NO 27
<211> LENGTH: 18
<212> TYPE: DNA
<213> ORGANISM: Homo sapiens

<400> SEQUENCE: 27
actgtgaggc agcactcg                                              18

<210> SEQ ID NO 28
<211> LENGTH: 18
<212> TYPE: DNA
<213> ORGANISM: Homo sapiens

<400> SEQUENCE: 28
cttctgctcc ccaaaacc                                              18

<210> SEQ ID NO 29
<211> LENGTH: 18
<212> TYPE: DNA
<213> ORGANISM: Homo sapiens

<400> SEQUENCE: 29
ctccttccac ccgtcagt                                              18

<210> SEQ ID NO 30
<211> LENGTH: 19
<212> TYPE: DNA
<213> ORGANISM: Homo sapiens

<400> SEQUENCE: 30
gccttccaag ggtctctac                                             19

<210> SEQ ID NO 31
<211> LENGTH: 17
```

```
<212> TYPE: DNA
<213> ORGANISM: Homo sapiens

<400> SEQUENCE: 31
ccgtccctct gtctcag                                               17

<210> SEQ ID NO 32
<211> LENGTH: 19
<212> TYPE: DNA
<213> ORGANISM: Homo sapiens

<400> SEQUENCE: 32
gctcccagga ctgacttct                                             19

<210> SEQ ID NO 33
<211> LENGTH: 20
<212> TYPE: DNA
<213> ORGANISM: Homo sapiens

<400> SEQUENCE: 33
gggctccact acttccactt                                            20

<210> SEQ ID NO 34
<211> LENGTH: 96
<212> TYPE: DNA
<213> ORGANISM: Homo sapiens

<400> SEQUENCE: 34
ggggcggagg aaagcgcaaa gggaaaagca agaagtggaa agaaatcctg aagttccctc    60
acattagcca gtgtgaagac ctccgaagga ccatag                              96
```